United States Patent
Stauffacher et al.

(10) Patent No.: US 9,604,925 B2
(45) Date of Patent: *Mar. 28, 2017

(54) CLASS II HMG-COA REDUCTASE INHIBITORS AND METHODS OF USE

(71) Applicant: Purdue Research Foundation, West Lafayette, IN (US)

(72) Inventors: Cynthia Stauffacher, Lafayette, IN (US); Mark Alfred Lipton, Lafayette, IN (US); Mohamed Naguieb Seleem, West Lafayette, IN (US); Tim Jonathan Schmidt, Lafayette, IN (US); Calvin Nicklaus Steussy, Jr., Indianapolis, IN (US); Victor W Rodwell, West Lafayette, IN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/707,197

(22) Filed: May 8, 2015

(65) Prior Publication Data
US 2015/0239830 A1    Aug. 27, 2015

Related U.S. Application Data

(63) Continuation of application No. 13/836,743, filed on Mar. 15, 2013, now Pat. No. 9,073,832.

(60) Provisional application No. 61/637,091, filed on Apr. 23, 2012, provisional application No. 61/637,697, filed on Apr. 24, 2012.

(51) Int. Cl.
| | |
|---|---|
| A61K 31/60 | (2006.01) |
| A01N 37/36 | (2006.01) |
| C07C 307/00 | (2006.01) |
| C07C 311/29 | (2006.01) |
| A01N 41/06 | (2006.01) |
| A61K 31/603 | (2006.01) |

(52) U.S. Cl.
CPC ............ *C07C 311/29* (2013.01); *A01N 41/06* (2013.01); *A61K 31/603* (2013.01)

(58) Field of Classification Search
CPC ............................. C07C 311/21; A61K 31/603
USPC .............................. 514/159, 166; 564/88, 92
See application file for complete search history.

(56) References Cited

PUBLICATIONS

STN Registry RN-670266-33-8, 2004.*
CAS registry file, RN 1052461-52-5, 2008.
Hedl et al. "Inhibition of the Class II HMG-CoA reductase of Pseudomonas mevaloni," Protein Science, 2004, vol. 13, pp. 1693-1697.

* cited by examiner

*Primary Examiner* — Shengjun Wang
(74) *Attorney, Agent, or Firm* — Valauskas Corder LLC (57) ABSTRACT

Disclosed are compositions and methods for treating bacterial infections.

14 Claims, 5 Drawing Sheets

CLASS II HMG-COA REDUCTASE INHIBITORS AND METHODS OF USE

CROSS-REFERENCE TO RELATED APPLICATIONS

This application is a continuation of U.S. application Ser. No. 13/836,743, filed Mar. 15, 2013, which incorporated by reference in its entirety, and claims the benefit of priority to U.S. Provisional Application Nos. 61/637,091 filed Apr. 23, 2012 and 61/637,697 filed Apr. 24, 2012, each of which is incorporated by reference in its entirety.

STATEMENT REGARDING FEDERALLY SPONSORED RESEARCH OR DEVELOPMENT

Not applicable.

INTRODUCTION

Antibiotic resistant pathogenic bacteria such as vancomycin resistant *Enterococcus* (VRE), methicillin resistant *Staphylococcus aureus* (MRSA), and penicillin resistant *Streptococcus pneumoniae* (PRSP) are the most common causes of hospital-acquired (nosocomial) infections in the United States and Europe. Nosocomial infections cause tens of thousands of deaths annually and result in billions of dollars in additional health care costs in the U.S. alone. Antibiotics currently used to treat these infections frequently cause nausea, vomiting, and diarrhea. Because these antibiotics are not specific for the pathogenic bacteria and kill normal flora, i.e., commensal bacteria, treatment of infections often causes oral, intestinal, or genital infections due to fungal overgrowth. Furthermore, antibiotics used to treat antibiotic resistant bacteria, such as vancomycin, have adverse side effects, including nephrotoxicity.

There is a need in the art for new antibiotics effective in treating pathogenic microbial infections. The compositions and methods described herein address that need.

SUMMARY

The present invention relates generally to compositions and methods for treating infections by pathogenic bacteria.

In certain embodiments, the invention includes compounds having one of the following two structures:

wherein:
$R^1$ is a hydroxyl, alkoxy, or substituted alkoxy;
$R^2$ is H, alkyl, or substituted alkyl;
$R^4$ and $R^6$ are independently selected from alkyl substituents of the type $-(CH_2)_m-R^C$, wherein m=0-14, optionally having polar substituents such as OH, $NR^A R^B$, $OPO_3H_2$, $OSO_3H$, $PO_3H_2$, $SO_2H$, and $CO_2$, or a cyclohexyl or benzyl substituent, optionally having unsaturation and/or branching in the alkyl chain;
$R^5$=OH, $NR^A R^B$, or a halogen;
$R^A$ and $R^B$ are independently selected from $-(CH_2)_nH$, $-(CH_2)_nOH$, $-(CH_2)_n CH(CH_3)_2$, $-(CH_2)-C(CH_3)_3$, $-(CH_2)_n$-cyclohexyl, and $-(CH_2)_n$-phenyl, wherein n=0-3, $R^C$=H, OH, $NR^A R^B$, $OPO_3H_2$, $OSO_2H$, $PO_3H_2$, $SO_2H$, $CO_2$, $CH(CH_3)_2$, $C(CH_3)_3$, cyclohexyl, or phenyl;
X, Y, and Z are independently selected from N, CH, and $CR^5$, such that the core ring structure is selected from benzene, pyridine, pyrazine, pyridazine, and pyrimidine;
A, B, D, and E are independently selected from N, CH, and $CR^4$, such that the core ring structure is selected from benzene, pyridine, pyrazine, pyridazine, and pyrimidine, or Q=S, O, or $NR^A$ and U, V, and W are independently selected from N and $CR^5$, such that the core ring structure is selected from pyrrole, imidazole, pyrazole, furan, oxazole, isooxazole, thiophene, thiazole, and isothiazole.

In certain embodiments, the compound is provided as a pharmaceutically acceptable salt.

In certain embodiments, the compounds are provided as a pharmaceutical composition comprising one or more of the compounds and a pharmaceutically acceptable carrier.

In certain embodiments, the compounds are provided as a biocide having activity against biofilms and certain biofilm forming bacteria.

Advantageously, the compounds and pharmaceutical compositions have antibacterial activity against Gram-positive pathogens, while lacking antibacterial activity against Gram-negative commensal bacteria.

In certain embodiments, methods for treating a bacterial infection in a subject are provided. The methods involve administering a pharmaceutical composition of the invention in an amount effective to inhibit growth of or kill the bacteria.

DETAILED DESCRIPTION

The compositions described herein were designed to specifically inhibit Class II 3-hydroxy-3-methylglutaryl-coenzyme A reductase (II-HMGR), which catalyzes the conversion of HMG to mevalonate and is a rate-limiting enzyme in the mevalonate pathway. Certain Gram-positive cocci, including *S. aureus*, *E. faecalis*, and *S. pneumoniae*, rely exclusively on the mevalonate pathway for the production of isopentenyl pyrophosphate (IPP), a precursor required for cell wall synthesis. Knocking out the HMGR gene in Gram-positive bacteria causes the bacteria to become weak and to lose virulence, and to depend on an external source of mevalonate. In contrast, most Gram-negative bacteria, including most commensal bacteria, depend on an alternate pathway for IPP synthesis and lack II-HMGR. Inhibition of II-HMGR is advantageous because it allows specific targeting of Gram-positive pathogens over Gram-negative commensal bacteria.

notably the multidrug resistant *Staphylococcus aureus* and *Enterococcus faecalis* have the eukaryotic pathway with an HMG-CoA Reductase, though the active site is substantially different than the eukaryotic enzyme.

The mechanism of the reductase is to bind HMG-CoA and NADH to the surface of the molecule, bringing the nicotinamide ring of NADH and the C1 carbon close together. This binding causes changes in the active site, facilitating the reduction of the HMG-CoA by the NADH. The reduced NAD is replaced by a second NADH. A second reduction creates the final products, free CoA and mevalonate

All eukaryotes have a mevalonate pathway for the synthesis of IPP that employs Class I HMGR (I-HMGR). Inhibition of I-HMGR by statins is used to reduce cholesterol biosynthesis in humans. The active site of II-HMGR is substantially different than that of the eukaryotic enzyme. Because of these differences, the affinity of statins for I-HMGR is six orders of magnitude higher for I-HMGR than for II-HMGR. Exploitation of differences between the active sites of I-HMGRs and II-HMGRs allows for the design of inhibitors specific for II-HMGR.

As described in the examples below, it was discovered that 5-(N-(4-butylphenyl)sulfamoyl)-2-hydroxybenzoic acid (N-bsha or compound 1) inhibits HMGR-II. X-ray crystallographic studies reveal that N-bsha binds in the active site of class II HMGR and is competitive inhibitor of II-HMGR. Analogues of N-bsha were synthesized an evaluated for the ability to inhibit II-HMGR catalyzed conversion of HMG-CoA to mevalonate. Those analogues exhibiting inhibition of II-HMGR were tested for the ability to inhibit antibiotic resistant bacteria.

Figure 1:
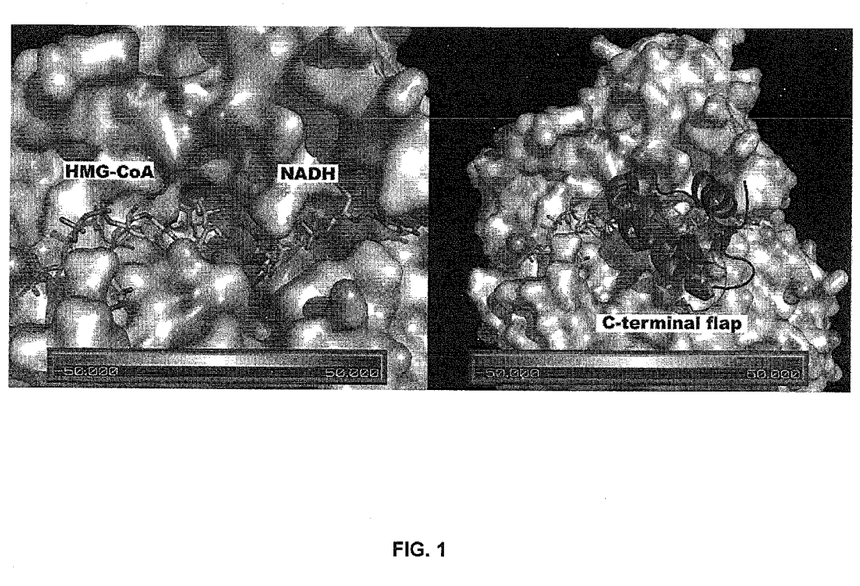
FIG. 1 shows binding of substrates in the active site of HMGR.

The active site of the enzyme is a groove on the surface of the molecule. As part of this binding, the active site becomes covered with a 50 residue 'flap' domain that serves to protect the intermediate products from hydrolysis (FIG. 1). The binding of the inhibitors of the present invention also closes the flap domain.

Figure 2:
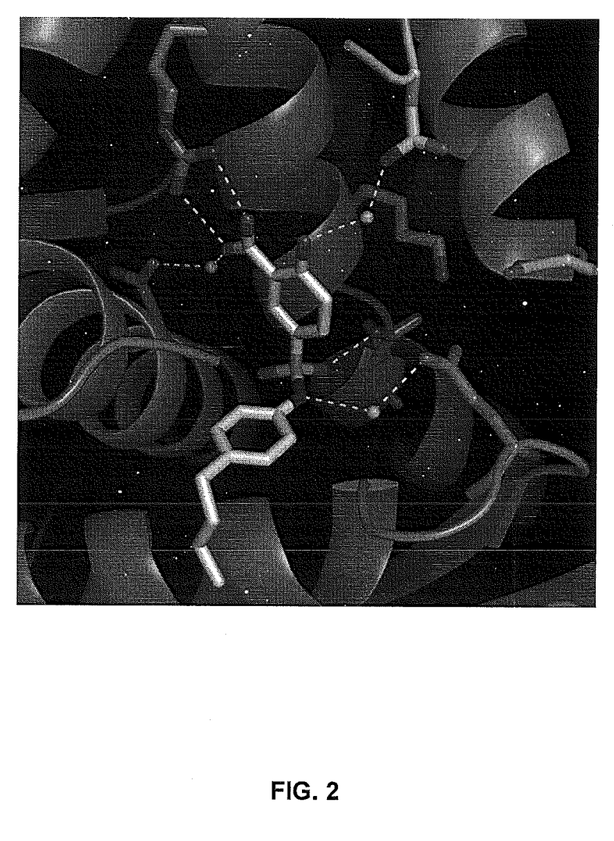
FIG. 2 shows binding of inhibitor N-bsha in the active site of HMGR.

The inhibitor first identified (N-bsha) binds in the pocket that ordinarily holds the HMG portion of the HMG-CoA reductase ligand (FIG. 2). The binding includes direct and water mediated hydrogen bonds around the benzoic acid portion of the inhibitor, and hydrophobic interactions around the benzene ring and alkane tail.

In certain embodiments, compounds according to the present invention have one of the two following structures:

wherein:
$R^1$=is a hydroxyl, alkoxy, or substituted alkoxy;
$R^2$=is H, alkyl, or substituted alkyl;
$R^4$ and $R^6$ are independently selected from alkyl substituents of the type —$(CH_2)_m$—$R^C$, wherein m=0-14, optionally having polar substituents such as OH, $NR^AR^B$, $OPO_3H_2$, $OSO_3H$, $PO_3H_2$, $SO_2H$, and $CO_2$, or a cyclohexyl or benzyl substituent, optionally having unsaturation and/or branching in the alkyl chain;

$R^5$=OH, $NR^AR^B$, or a halogen;

$R^A$ and $R^B$ are independently selected from —$(CH_2)_nH$, —$(CH_2)_nOH$, —$(CH_2)_nCH(CH_3)_2$, —$(CH_2)$—$C(CH_3)_3$, —$(CH_2)_n$-cyclohexyl, and —$(CH_2)_n$-phenyl, wherein n=0-3, $R^C$=H, OH, $NR^AR^B$, $OPO_3H_2$, $OSO_2H$, $PO_3H_2$, $SO_2H$, $CO_2$, $CH(CH_3)_2$, $C(CH_3)_3$, cyclohexyl, or phenyl;

X, Y, and Z are independently selected from N, CH, and $CR^5$, such that the core ring structure is selected from benzene, pyridine, pyrazine, pyridazine, and pyrimidine;

A, B, D, and E are independently selected from N, CH, and $CR^4$, such that the core ring structure is selected from benzene, pyridine, pyrazine, pyridazine, and pyrimidine, or Q=S, O, or $NR^A$ and U, V, and W are independently selected from N and $CR^5$, such that the core ring structure is selected from pyrrole, imidazole, pyrazole, furan, oxazole, isooxazole, thiophene, thiazole, and isothiazole.

In certain embodiments, $R^1$ is OH. In certain embodiments, $R^1$ is —O—(CO)$NH_2$, or —$OCH_2$(CO)$NH_2$.

In certain embodiments, $R^2$ is H.

In certain embodiments, the compound includes A, B, D, and E in a ring structure selected from the group consisting of benzene, pyridine, pyrazine, pyridazine, and pyrimidine. In certain embodiments, the compound includes A, B, D, and E in a benzene ring structure.

Extending the carbon tail ($R^4$ or $R^6$) or adding hydrophobic (phenyl or hexane) groups to the carbon tail of the inhibitors of the present invention has been found to lead to greater inhibition of II-HMGR.

In certain embodiments, the compound includes Q, U, V, and W in a ring structure selected from pyrrole, imidazole, pyrazole, furan, oxazole, isooxazole, thiophene, thiazole, and isothiazole.

In certain embodiments, the compound includes A, B, D, and E in a ring structure selected from the group consisting of benzene, pyridine, pyrazine, pyridazine, and pyrimidine, and $R^4$ is an alkyl substituent of the type —$(CH_2)_mH$, wherein m is 0, 1, 2, 3, 4, 5, 6, 7, 8, 9, 10, 11, 12, 13, or 14. In some embodiments, the alkyl substituent is a branched alkyl chain with from 4 to 14 carbon atoms. In some embodiments, the alkyl substituent is at least partially unsaturated, i.e., comprises one or more alkenyl and/or alkynyl groups.

In certain embodiments, the compound includes Q, U, V, and W in a ring structure selected from pyrrole, imidazole, pyrazole, furan, oxazole, isooxazole, thiophene, thiazole, and isothiazole and $R^6$ is an alkyl substituent of the type —$(CH_2)_mH$, wherein m is 0, 1, 2, 3, 4, 5, 6, 7, 8, 9, 10, 11, 12, 13, or 14. In some embodiments, the alkyl substituent is a branched alkyl chain with from 4 to 14 carbon atoms. In some embodiments, the alkyl substituent is at least partially unsaturated, i.e., comprises one or more alkenyl and/or alkynyl groups.

In certain embodiments, $R^4$ or $R^6$ are $C_6H_{13}$, $C_7H_{15}$, $C_{10}H_{21}$, $C_{12}H_{25}$, $(CH_2)_3CH(CH_3)_2$, $(CH_2)_4CH(CH_3)_2$, or $(CH_2)c$-$C_6H_{11}$.

In certain embodiments, II-HMGR inhibitors kill or inhibit the growth of Gram-positive pathogens, e.g., MRSA and/or VRE, without affecting the growth of commensal Gram-negative bacteria, e.g., *Escherichia coli*.

In certain embodiments, the II-HMGR inhibitors selectively inhibit II-HMGR over I-HMGR, with at least a 100-fold greater inhibitory activity against II-HMGR vs. I-HMGR.

The inhibitors of the present invention may be formulated as a pharmaceutical composition suitable for administration by any suitable mode of administration, including, for example orally (e.g., enterally or sublingually), intravenously, intramuscularly, subcutaneously, transdermally, vaginally, rectally, intranasally, and the like.

In certain embodiments, inhibitors of the invention are prepared, purified, or formulated as a corresponding salt of the active compound or prodrug, for example, a pharmaceutically-acceptable salt. Examples of pharmaceutically acceptable salts are discussed in Berge, et al., J. Pharm. Sci., 66, 1-19 (1977). Unless otherwise specified, a reference to a particular compound also includes salt forms thereof. The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

In certain embodiments, compositions of the present invention comprise a II-HMGR inhibitor and a pharmaceutically acceptable excipient, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, e.g., having an undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

In certain embodiments, the compounds of the invention may be formulated for use as a bacteriocidal composition for use on surfaces that tend to serve as a support for biofilms, e.g., catheters. The bacteriocidal compositions include the compound and, for example, a suitable carrier. The bacteriocidal compositions may be provided in a form comprising the II-HMGR inhibitor in a concentration effective to kill or inhibit the growth of bacteria, or conveniently may be supplied in a concentrated form to be diluted prior to use.

The following non-limiting examples are intended to be purely illustrative.

EXAMPLES

Screening of Compounds Inhibition of II-HMGR

A library of 300,000 compounds was screened against *E. faecalis* II-HMGR to identify II-HMGR inhibitors. Compounds were screened for the ability to inhibit *E. faecalis* II-HMGR from the mevalonate to HMG-CoA direction by measuring changes in NADPH using absorbance at 340 nm. Among the compounds screened, 5-(N-(4-butylphenyl)sulfamoyl)-2-hydroxybenzoic acid 1 (N-bsha) was found to be the best inhibitor of II-HMGR, with an $IC_{50}$ of 5 µM.

Design of the Modified HMGR Inhibitors

The X-ray crystal structure of *E. faecalis* HMGR complexed with inhibitor 1 shows that the hydrophobic para-butyl group occupies a hydrophobic pocket in the active site that normally accommodates the pantothenic acid portion of HMG CoA. Initial investigation of an analogue of 1 lacking the butyl "tail" indicated that an aliphatic moiety may be important for inhibition of HMGR. A series of analogues of 1 was synthesized (2a-m) in which the aliphatic tail was varied, as show in FIG. 3. In analogues 2a-h, the length of the linear alkyl chain was varied from 2 to 14 carbon atoms; in 2i-k, the aliphatic chain has terminal branching, and in 2l and 2m cyclohexyl and phenyl rings, respectively, terminate the aliphatic tail. It was envisaged that increased hydrophobic character in the tail may increase affinity for the HMGR active site, provided that the tail can be accommodated within the active site.

Examination of the HMGR co-crystal structure with 1 also revealed the presence of a water-mediated hydrogen bond between the phenolic hydroxyl of 1 and the Asn213 residue of HMGR, which is known to form hydrogen bonds to the NADPH cofactor in the co-crystal structure of HMGR with a substrate analogue. To displace the bound water molecule, analogue 3 was designed in which the phenolic hydroxyl is alkylated with an acetamide substituent with the intention of engaging Asn213 in a cooperative hydrogen bond between the two primary amides.

Synthesis of the Modified Inhibitors

All starting materials were purchased from Sigma Aldrich (St. Louis, Mo., USA), TCI America (Portland, Oreg., USA) or VWR (VWR Direct, Arlington Heights, Ill., USA). All solvents were dried by passage through an activated column composed of activated alumina and supported copper redox catalyst reactant, prior use. To analyze compounds purity, reverse phase HPLC (RP-HPLC) was performed using a Gilson instrument and Vydac C-8 column, with HPLC grade acetonitrile and deionized water and 0.1% trifluoroacetic acid. Flash chromatography was performed using 230-400 mesh silica gel or prep-HPLC was used to purify compounds. Proton NMR spectra were obtained on a Varian Inova-300 or a Bruker ARX-400 spectrometer at 300 MHz and 400 MHz, respectively.

The target molecules were synthesized using well-established chemistry (Scheme 1). Commercially available 1-iodo-4-nitrobenzene (4) was coupled with terminal alkynes using Sonogashira coupling, forming phenylalkynes 6a-m in high yields. Simultaneous reduction of alkyne and nitro groups by catalytic hydrogenation over platinum oxide afforded substituted anilines 7a-m. The only exception was 4-propylaniline (7b), which was commercially available. Each aniline was reacted with methyl 5-(chlorosulfonyl)-2-hydroxybenzoate (8), synthesized according to a literature protocol, under Schotten-Baumann conditions to afford sulfonamides which were saponified to afford the target molecules (2a-m). As a control, the lead compound 1 was synthesized from commercially available p-butylaniline using this same protocol.

Scheme 1: General synthesis of class II-HMGR inhibitors[a]

[a]Reagents and conditions: (i) CuI, (PPh$_3$)Cl$_2$ (0.1 eq.), TEA, THF, 2 h; (ii) H$_2$, PtO$_2$, Ethanol, 2 h.; (iii) 8, NEt$_3$, CH$_2$Cl$_2$, 18 h; (iv) NaOH, THF—MeOH—H$_2$O (1:1:1), 18 h.

The synthesis of the ether 3, is shown in Scheme 2. The sulfonamide 9, previously made as an intermediate during our synthesis of lead compound 1, was alkylated on the phenolic hydroxyl with iodoacetamide under basic conditions to afford the ether 10. Saponification of the methyl ester of 10 afforded the desired target 3.

Scheme 2: Synthesis of ether 3[a]

[a]Reagents and conditions: (i) NaHCO$_3$, Dioxane/Water (1:1), rt. 5 h, 90%; (ii) iodoacetamide, Cs$_2$CO$_3$, Acetone, rt. 18 h, 31%; (iii) NaOH, THF/MeOH/H$_2$O (1:1:1), rt. 18 h, 99%.

Methyl 5-(chlorosulfonyl)-2-hydroxybenzoate (6)

Salicylic acid (3.00 g, 21.7 mmol) was dissolved in MeOH (50 mL) and H$_2$SO$_4$ (6 mL) was added dropwise to the stirring solution. The resultant solution was heated to reflux for 18 h and, after cooling to room temperature, the solvent was removed under reduced pressure. The residue was diluted with H$_2$O (10 mL) and extracted with CH$_2$Cl$_2$ (3×10 mL). The combined organic layers were washed sequentially with saturated aqueous NaHCO$_3$ (10 mL), brine (10 mL) and water (10 mL), dried over Na$_2$SO$_4$, and concentrated under reduced pressure. The crude methyl salicylate was obtained in 85% as a colorless oil (2.80 g) and used without further purification. $^1$H NMR (300 MHz, CDCl$_3$) δ 10.7 (s, 1H), 7.84 (d, J=7.5 Hz, 1H), 7.47 (t, J=8.1 Hz, 1H), 6.99 (d, J=8.1 Hz, 1H), 6.90 (t, J=8.1 Hz, 1H) ppm.

To a solution of SOCl$_2$ (1.34 mL, 18.4 mmol) and ClSO$_3$H acid (4.92 mL, 73.6 mmol) cooled to −10° C. was added slowly the crude methyl salicylate. The reaction was stirred at room temperature for 18 h, after which the brown reaction was poured slowly over ice (10 mL) that was placed in an ice bath and continually stirred with a glass rod until the resultant precipitate turned colorless. The precipitate was filtered under vacuum and washed with cold water. The sulfonyl chloride 6 was obtained as a colorless solid (4.18 g, 91% yield). $^1$H NMR (300 MHz, CDCl$_3$) δ 11.55 (s, 1H), 8.56 (d, J=2.1 Hz, 1H), 8.10 (dd, 2.4, 9.0 Hz, 1H), 7.19 (d, J=9.0 Hz, 1H), 4.04 (s, 3H) ppm. $^{13}$C NMR (100 MHz, CDCl$_3$) δ 168.9, 166.4, 134.9, 133.5, 130.5, 119.3, 112.5, 53.1 ppm.

General Procedure for Sonogashira Reaction

In a round bottom flask under nitrogen, 1-iodo-4-nitrobenzene (3, 300 mg, 1.20 mmol), freshly recrystallized CuI (28.8 mg, 0.120 mmol) and Pd(PPh$_3$)$_2$Cl$_2$ (42.1 mg, 0.06 mmol) were dissolved in THF (5.0 mL). The terminal alkyne 2 (1.4 mmol) was added dropwise to the solution, which gradually turned bright yellow. To the resultant solution NEt$_3$ (0.68 mL, 4.84 mmol, 4.0 eq.) was added slowly, during which time the reaction became dark brown. After 2 h, the reaction was diluted with water (5 mL) and extracted with CH$_2$Cl$_2$ (3×5 mL). The combined organic layers were washed with brine (5 mL) and water (5 mL), dried over Na$_2$SO$_4$ and concentrated under reduced pressure. The product arylalkynes 4 were purified by flash chromatography using 100% hexanes.

1-Ethynyl-4-nitrobenzene (4a). TMS-protected 4a was obtained as a colorless, crystalline solid (279 mg, 99%); $^1$H NMR (300 MHz, CDCl$_3$) δ 8.15 (d, J=8.7 Hz, 2H), 7.58 (d, J=9.0 Hz, 2H), 0.25 (s, 9H) ppm. $^{13}$C NMR (75 MHz, CDCl$_3$) δ 146.9, 132.5, 129.8, 123.3, 102.5, 100.4, 85.7, −0.43 ppm. Deprotection was done by dissolving 4a (279 mg, 1.30 mmol) in 3:1 THF-MeOH (4 mL) and adding potassium carbonate (528 mg, 3.82 mmol) slowly. The reaction was stirred for 2 h, after which the mixture was diluted with Et$_2$O, washed with saturated NH$_4$Cl and H$_2$O, dried with MgSO$_4$ and concentrated under reduced pressure. The resultant terminal alkyne 4a (129 mg, 68%) was then used with no further purification. $^1$H-NMR (300 MHz, CDCl$_3$) δ 8.19 (d, J=8.4 Hz, 2H), 7.64 (d, J=8.7 Hz, 2H), 3.36 (s, 1H) ppm. $^{13}$C NMR (75 MHz, CDCl$_3$) δ 147.3, 132.8, 128.7, 123.4, 53.3 ppm.

1-Nitro-4-(1-pentynyl)benzene (4b) was obtained as a brown oil (148 mg, 65%); $^1$H-NMR (300 MHz, CDCl$_3$) δ 8.15 (d, J=8.7 Hz, 2H), 7.52 (d, J=9.0 Hz, 2H), 2.42 (t, 2H), 1.68-1.61 (m, 2H), 1.05 (t, 3H) ppm. $^{13}$C NMR (75 MHz, CDCl$_3$) δ 132.1, 131.7, 131.1, 123.3, 96.4, 79.3, 21.7, 21.4, 13.4. ppm 1-(1-Hexynyl)-4-nitrobenzene (4c) was obtained as an amber oil (241 mg, 99%). $^1$H-NMR (300 MHz, CDCl$_3$) δ 8.14 (d, J=9.3 Hz, 2H), 7.49 (d, J=8.7 Hz, 2H), 2.43 (t, J=7.5 Hz, 2H), 1.64-1.42 (m, 4H), 0.94 (t, J=6.9 Hz, 3) ppm. $^{13}$C NMR (75 MHz, CDCl$_3$) δ 146.4, 132.1, 131.1, 123.3, 96.6, 79.1, 30.3, 21.9, 19.1, 13.4 ppm.

1-(1-Heptynyl)-4-nitrobenzene (4d) was obtained as a brown oil (234.6 mg, 90%). $^1$H-NMR (300 MHz, CDCl$_3$) δppm 8.13 (d, J=9.0 Hz, 2H), 7.49 (d, J=9.0 Hz, 2H), 2.41 (t, J=6.9 Hz, 2H), 1.65-1.55 (m, 2H), 1.46-1.28 (m, 4H), 0.90 (t, J=7.2 Hz, 3H). $^{13}$C NMR (75 MHz, CDCl$_3$) δ146.4, 132.1, 131.1, 123.3, 96.7, 79.1, 31.0, 27.9, 22.1, 19.4, 13.8.

1-(1-Decynyl)-4-nitrobenzene (4e) was obtained as a yellow oil (131 mg, 42%); $^1$H-NMR (300 MHz, CDCl$_3$) δ 8.14 (d, J=8.7 Hz, 2H), 7.50 (d, J=8.4 Hz, 2H), 2.42 (t, J=7.2 Hz, 2H), 1.63-1.58 (m, 2H), 1.43 (m, 2H), 1.28 (m, 8H), 0.87 (t, J=6.3 Hz, 3H) ppm. $^{13}$C NMR (75 MHz, CDCl$_3$) δ 146.4, 132.1, 131.1, 123.3, 96.7, 79.1, 31.7, 29.0, 28.9, 28.8, 28.2, 22.5, 19.4, 13.9 ppm.

1-(1-Dodecynyl)-4-nitrobenzene (4f)

Obtained as a brown oil (216 mg, 63%); $^1$H-NMR (300 MHz, CDCl$_3$) δ 8.14 (d, J=9.0 Hz, 2H), 7.50 (d, J=8.7 Hz, 2H), 2.42 (t, J=6.9 Hz, 2H), 1.63-1.55 (m, 2H), 1.45-1.40 (m, 2H), 1.25 (m, 12H), 0.86 (t, J=6.9 Hz, 3H) ppm. $^{13}$C NMR (75 MHz, CDCl$_3$) δ 146.4, 132.1, 131.1, 123.3, 96.7, 79.1, 31.8, 29.4, 29.2, 29.0, 28.8, 28.3, 22.5, 19.4, 14.0 ppm.

1-Nitro-4-(tetradec-1-yn-1-yl)benzene (4g) was obtained as a yellow solid (344 mg, 99%); $^1$H-NMR (300 MHz, CDCl$_3$) δ 8.13 (d, J=9.0 Hz, 2H), 7.48 (d, J=9.0 Hz, 2H), 2.41 (t, J=6.9 Hz, 2H), 1.62-1.57 (m, 2H), 1.44-1.38 (m, 2H), 1.24 (m, 16H), 0.86 (t, J=6.9 Hz, 3H) ppm. $^{13}$C NMR (75 MHz, CDCl$_3$) δ 146.3, 132.0, 131.1, 123.3, 96.6, 79.1, 31.8, 29.5, 29.4, 29.3, 29.0, 28.8, 28.3, 22.6, 19.4, 13.9 ppm.

1-(4-Methylpent-1-ynyl)-4-nitrobenzene (4h) was obtained as a brown oil (187 mg, 77%); $^1$H-NMR (300 MHz, CDCl$_3$) δ 8.14 (d, J=9.0 Hz, 2H), 7.50 (d, J=8.7 Hz, 2H), 2.33 (d, J=6.3 Hz, 2H), 1.96-1.87 (m, J=6.6 Hz, 1H), 1.04 (d, J=6.6 Hz, 6H) ppm. $^{13}$C NMR (75 MHz, CDCl$_3$) δ 146.4, 132.1, 131.1, 123.3, 95.6, 80.1, 28.5, 27.9, 21.9 ppm.

1-(5-Methylhex-1-ynyl)-4-nitrobenzene (4i) was obtained as a light brown oil (232 mg, 87%); $^1$H-NMR (300 MHz, CDCl$_3$) δ 8.15 (d, J=8.4 Hz, 2H), 7.51 (d, J=7.5 Hz, 2H), 2.44 (t, 2H), 1.76-1.70 (m, 1H), 1.55-1.48 (m, 2H), 0.95 (d, J=6.6 Hz, 6H) ppm. $^{13}$C NMR (75 MHz, CDCl$_3$) δ 146.4, 132.1, 131.1, 123.3, 96.7, 79.1, 37.2, 27.2, 22.0, 17.5 ppm.

1-(3,3-Dimethylbut-1-ynyl)-4-nitrobenzene (4j) was obtained as a bright yellow solid (91.1 mg, 37%); $^1$H-NMR (300 MHz, CDCl$_3$) δ 8.23 (d, J=7.8 Hz, 1H), 8.16 (d, J=7.5 Hz, 1H), 7.50-7.46 (dd, J=3.3, 7.8, 4.2 Hz, 2H), 1.34 (s, 9H) ppm. $^{13}$C NMR (100 MHz, CDCl$_3$) δ 142.7, 131.7, 125.5, 122.0, 100.9, 79.1, 30.8, 30.7, 28.0 ppm.

1-Nitro-4-(phenylethynyl)benzene (4k) was obtained as a bright yellow solid (239 mg, 89%); $^1$H-NMR (300 MHz, CDCl$_3$) δ 8.20 (d, J=8.7 Hz, 2H), 7.65 (d, J=8.4 Hz, 2H), 7.57-7.54 (dd, J=6.3, 1.8, 3.3 Hz, 2H), 7.40-7.37 (m, 3H) ppm. $^{13}$C NMR (75 MHz, CDCl$_3$) δ 146.8, 132.1, 131.7, 129.2, 128.5, 123.5, 122.0, 94.6, 87.5 ppm.

1-(Cyclohexylethynyl)-4-nitrobenzene (4l) was obtained as a brown oil (284 mg, 99%); $^1$H-NMR (300 MHz, CDCl$_3$) δ 8.11 (d, J=9.0 Hz, 2H), 7.48 (d, J=7.5 Hz, 2H), 2.63-2.54 (m, 1H), 1.87-1.82 (m, 2H), 1.75-1.67 (m, 2H), 1.55-1.46 (m, 2H), 1.39-1.22 (m, 4H) ppm. $^{13}$C NMR (75 MHz, CDCl$_3$) δ 146.3, 132.1, 131.1, 123.3, 100.5, 79.1, 32.9, 29.6, 25.6, 24.7 ppm.

General Procedure for Hydrogenation of 4a-m.

In a 100 mL round bottom flask, alkyne 4 (1.24 mmol) was dissolved in EtOH (6 mL), PtO$_2$, 83% Pt (40 mg, 0.18 mmol) was added, the solvent was degassed under reduced pressure and hydrogen gas was introduced by balloon. The reaction was stirred at for 2 h and filtered through Celite. The Celite pad was washed with CH$_2$Cl$_2$, EtOAc and MeOH, the filtrate was concentrated under reduced pressure and purified by flash chromatography using 5% EtOAc-hexanes to afford the aniline 5.

4-Ethylaniline (5a) was obtained as a colorless solid (110 mg, 46%); $^1$H-NMR (300 MHz, CDCl$_3$) δ 7.05 (d, J=8.4 Hz, 2H), 6.68 (d, J=8.4 Hz, 2H), 3.80 (br s, 2H), 2.58 (q, J=7.5 Hz, 2H), 1.24 (t, J=7.5 Hz, 3H) ppm. $^{13}$C NMR (75 MHz, CDCl$_3$) δ 144.0, 134.3, 128.5, 115.2, 27.9, 15.9 ppm.

4-Pentylaniline (5b) was obtained as a yellow brown oil (35./2 mg, 98%); $^1$H-NMR (300 MHz, CDCl$_3$) δ 6.99 (d, J=8.4 Hz, 2H), 6.64 (d, J=8.4 Hz, 2H), 3.63 (br s, 2H), 2.53 (t, J=8.1 Hz, 2H), 1.62-1.52 (m, J=6.9 Hz, 2H), 1.34-1.27 (m, 4H), 0.89 (t, J=7.2 Hz, 3H) ppm. $^{13}$C NMR (75 MHz, CDCl$_3$) δ 143.9, 133.5, 129.0, 115.1, 34.9, 31.4, 22.5, 13.9 ppm.

4-Hexylaniline (5c) was obtained as a pale amber oil (120 mg, 81%); $^1$H-NMR (300 MHz, CDCl$_3$) δ 7.04 (d, J=8.4 Hz, 2H), 6.67 (d, J=8.4 Hz, 2H), 3.52 (s, 2H), 2.56 (t, J=8.1 Hz, 2H), 1.64-157 (m, 2H), 1.42-1.33 (m, 6H), 0.95 (t, J=6.6 Hz, 3H) ppm. $^{13}$C NMR (75 MHz, CDCl$_3$) δ 143.9, 133.0, 129.0, 115.1, 35.0, 31.7, 28.9, 22.6, 14.1 ppm.

4-Heptylaniline (5d) was obtained as a pale brown oil (139 mg, 99%); $^1$H-NMR (300 MHz, CDCl$_3$) δ 7.02 (d, J=7.8 Hz, 2H), 6.66 (d, J=8.1 Hz, 2H), 3.47 (br s, 2H), 2.54 (t, J=8.1 Hz, 2H), 1.63-1.55 (m, 2H), 1.35-1.28 (m, 8H), 0.93 (t, J=7.5 Hz, 3H). $^{13}$C NMR (75 MHz, CDCl$_3$) δ 143.9, 133.0, 129.0, 115.1, 35.0, 31.8, 29.2, 22.6, 14.0 ppm.

4-Decylaniline (5e) was obtained as a yellow solid crystals (145 mg, 99%); $^1$H-NMR (300 MHz, CDCl$_3$) δ 7.00 (d, J=7.8 Hz, 2H), 6.65 (d, J=8.4 Hz, 2H), 3.63 (broad s, 2H), 2.51 (t, J=8.1 Hz, 2H), 1.59-1.55 (m, 2H), 1.28 (s, 14H), 0.91 (t, J=6.9 Hz, 3H) ppm. $^{13}$C NMR (75 MHz, CDCl$_3$) δ 143.9, 133.0, 129.0, 115.1, 35.0, 31.8, 29.5, 29.2, 22.6, 14.0 ppm.

4-Dodecylaniline (5f) was obtained as a yellow oil (198 mg, 99%); $^1$H-NMR (300 MHz, CDCl$_3$) δ 7.01 (d, J=7.5 Hz, 2), 6.65 (d, J=8.1 Hz, 2H), 3.59 (broad s, 2H), 2.54-2.50 (t, J=6.9 Hz, 2H), 1.58 (m, 2H), 1.29 (m, 16H), 0.92 (t, 3H) ppm. $^{13}$C NMR (75 MHz, CDCl$_3$) δ143.9, 133.0, 129.0, 115.1, 35.0, 31.9, 31.8, 29.6, 29.3, 22.6, 14.1 ppm.

4-Tetradecylaniline (5g) was obtained as a pale gray solid (250 mg, 71%); $^1$H-NMR (300 MHz, CDCl$_3$) δ 7.03 (d, J=7.8 Hz, 2H), 6.67 (d, J=8.1 Hz, 2H), 3.55 (br s, 2H), 2.55 (t, J=7.8 Hz, 2H), 1.63-1.58 (m, 2H), 1.32 (m, 22H), 0.95 (t, J=7.2 Hz, 3H). $^{13}$C NMR (75 MHz, CDCl$_3$) δ 143.9, 133.0, 129.0, 115.1, 35.0, 31.9, 31.8, 29.6, 29.5, 29.4, 29.3, 22.6, 14.1.

4-(4-Methylpentyl)aniline (5h) was obtained as a colorless solid (176 mg, 99%); $^1$H-NMR (300 MHz, CDCl$_3$) δ 7.04 (d, J=7.8 Hz, 2H), 6.68 (d, J=8.1 Hz, 2H), 3.60 (broad s, 2H), 2.54 (t, J=7.8 Hz, 2H), 1.64-1.57 (m, 3H), 1.30-1.23 (m, J=8.4 Hz 2H), 0.95 (d, J=7.2 Hz, 6H) ppm. $^{13}$C NMR (75 MHz, CDCl$_3$) δ 144.8, 133.0, 129.1, 115.1, 38.6, 35.3, 29.6, 27.8, 22.6 ppm.

4-(5-Methylhexyl)aniline (5i) was obtained as an orange oil (173 mg, 86%); $^1$H-NMR (300 MHz, CDCl$_3$) δ 7.05 (d, J=8.4 Hz, 2H), 6.68 (d, J=8.1 Hz, 2H), 3.61 (br s, 2H), 2.57 (t, J=7.8 Hz, 2H), 1.56-1.66 (m, 3H), 1.35-1.44 (m, 2H), 1.23-1.30 (m, 2H), 0.95 (d, J=6.3 Hz, 6H) ppm. $^{13}$C NMR (75 MHz, CDCl$_3$) δ 143.9, 133.0, 129.1, 115.2, 38.8, 35.1, 32.1, 27.9, 27.0, 22.6 ppm.

4-(3,3-Dimethylbutyl)aniline (5j) was obtained as a brown solid (51 mg, 64%); $^1$H-NMR (300 MHz, CDCl$_3$) δ 7.00 (d, J=8.4 Hz, 2H), 6.64 (d, J=8.4 Hz, 2H), 3.47 (br s, 2H), 2.41-2.50 (m, 2H), 1.43-1.49 (m, 2H), 0.96 (s, 9H)

ppm. $^{13}$C NMR (75 MHz, CDCl$_3$) δ 143.8, 133.5, 128.9, 115.2, 46.6, 30.4, 30.1, 29.6, 29.3 ppm.

4-(2-Phenylethyl)aniline (5k) was obtained as a pale yellow solid (192 mg, 91%); $^1$H-NMR (300 MHz, CDCl$_3$) δ 7.42 (t, J=7.5, 7.2 Hz, 2H). 7.33 (t, J=4.2, 7.5 Hz, 3H), 7.12 (d, J=7.8 Hz, 2H), 6.73 (d, J=7.8 Hz, 2H), 3.59 (br s, 2H), 2.94-3.04 (m, 4H) ppm. $^{13}$C NMR (75 MHz, CDCl$_3$) δ144.4, 142.1, 131.8, 129.2, 128.6, 128.4, 125.8, 115.3, 38.4, 37.2 ppm.

4-(2-Cyclohexylethyl)aniline (5l) was obtained as a brown oil (261 mg, 99%); $^1$H-NMR (300 MHz, CDCl$_3$) δ 7.06 (d, J=7.8 Hz, 2H), 6.68 (d, J=8.4 Hz, 2H), 3.60 (br s, 2H), 2.59 (t, 2H), 1.76-1.86 (m, 5H), 1.50-1.57 (m, 2H), 1.21-1.36 (m, 4H), 0.95-1.06 (m, 2H). $^{13}$C NMR (75 MHz, CDCl$_3$) δ 143.8, 133.3, 129.0, 115.3, 39.7, 37.2, 33.3, 32.3, 26.7, 26.3 ppm.

General Procedures for the Synthesis of Analogues 2a-m.

Method A: Aniline 5 (0.80 mmol) was dissolved in CH$_2$Cl$_2$ (8.0 mL) and sulfonyl chloride 6 (0.80 mmol) was added slowly, followed by the slow addition of NEt$_3$ (0.40 mmol). The resultant mixture was stirred for 15 to 18 hours, diluted with water (5 mL) and washed with CH$_2$Cl$_2$ (3×5 mL). The combined organic layers were washed with brine (5 mL) and H$_2$O (5 mL), dried over Na$_2$SO$_4$ and concentrated under reduced pressure.

The residue was dissolved in THF-MeOH—H$_2$O (1:1:1) and crushed pellets of NaOH (20.0 mg, 0.50 mmol) were added to the stirring solution. After 18 h, the reaction mixture was concentrated under reduced pressure, diluted with H$_2$O (5 mL) and washed with EtOAc (3×5 mL). The combined organic layers were washed with water (5 mL), dried over Na$_2$SO$_4$ and concentrated under reduced pressure. The products were purified by preparative reverse phase HPLC.

Method B: To an aqueous NaHCO$_3$ solution (2.0 mL, 5.0 M, 0.44 mmol) was added the aniline 5 (0.22 mmol) and 1,4-dioxane (1.0 mL). The biphasic mixture was stirred vigorously at 0° C. and a solution of sulfonyl chloride 6 (54.0 mg, 0.22 mmol) in 1,4-dioxane (1 mL) was added to the reaction dropwise at 0° C. The reaction was warmed to room temperature and stirred for 18 h, after which the reaction mixture was concentrated under reduced pressure, diluted with H$_2$O (5 mL) and extracted with EtOAc (3×5 mL). The combined organic layers were washed with brine (5 mL) and H$_2$O (5 mL), dried over Na$_2$SO$_4$ and concentrated under vacuum.

The crude product was dissolved in THF-MeOH—H$_2$O (1:1:1) (3 mL) and crushed pellets of NaOH (20.0 mg, 0.50 mmol) were added to the stirring solution. After 18 h, the reaction mixture was concentrated under reduced pressure, diluted with H$_2$O (5 mL) and extracted with EtOAc (3×5 mL). The combined organic layers were washed with H$_2$O (5 mL), dried over Na$_2$SO$_4$ and concentrated under reduced pressure. The crude product was purified by preparative reverse phase HPLC.

5-[N-(4-butylphenyl)sulfamoyl]-2-hydroxybenzoic acid (1), synthesized using Method A, was obtained as a colorless powder (99.4 mg, 71%); $^1$H-NMR (300 MHz, CD$_3$OD) δ 8.28 (d, J=2.4 Hz, 1H), 7.58-7.54 (dd, J=2.4, 9.0, 2.1 Hz, 1H), 7.02-6.95 (m, 4H), 6.81 (d, J=9.0 Hz, 1H), 2.52 (t, 2H), 1.56-1.46 (m, 2H), 1.32-1.25 (m, 2H), 0.92 (t, 3H) ppm. $^{13}$C NMR (100 MHz, CD$_3$OD) δ 173.9, 166.7, 140.6, 136.5, 132.9, 131.7, 130.1, 129.9, 129.6, 122.9, 119.4, 117.8, 35.8, 34.7, 23.2, 14.2 ppm.

5-[N-(4-ethylphenyl)sulfamoyl]-2-hydroxybenzoic acid (2a), synthesized using Method A, was obtained as an off-white powder (69.6 mg, 62%); $^1$H-NMR (300 MHz, CD$_3$OD) δ 8.28 (d, J=2.1 Hz, 1H), 7.57 (dd, J=2.7, 8.7, 3.0 Hz, 1H), 6.95-7.03 (m, 5H), 6.81 (d, J=9.0 Hz, 1H), 2.51 (q, 2H), 1.91 (s, 1H), 1.12 (t, 3H) ppm. $^{13}$C NMR (100 MHz, CD$_3$OD) δ 180.7, 174.3, 142.2, 136.3, 132.7, 131.7, 129.4, 123.0, 120.1, 117.9, 108.9, 30.1, 29.1, 24.3, 16.1 ppm.

2-hydroxy-5-[N-(4-propyl phenyl)sulfamoyl]benzoic acid (2b), synthesized using Method A, was obtained as a pink powder (178 mg, 19%); $^1$H-NMR (300 MHz, CD$_3$OD) δ 8.17 (d, J=2.4 Hz, 1H), 7.77 (dd, J=2.7, 8.7, 2.7 Hz, 1H), 7.00 (dd, J=8.7, 11.7, 8.7 Hz, 4H), 6.98 (d, 1H) ppm. $^{13}$C NMR (100 MHz, CD$_3$OD) δ 172.3, 166.2, 140.9, 136.3, 134.8, 131.6, 131.3, 130.1, 123.2, 118.9, 113.8, 38.2, 25.5, 13.9 ppm.

2-hydroxy-5-[N-(4-pentylphenyl)sulfamoyl]benzoic acid (2c), synthesized using Method B, was obtained as a pale orange powder (83.7 mg, 99%); $^1$H-NMR (300 MHz, CD$_3$OD) δ 8.29 (d, J=2.4 Hz, 1H), 7.51 (dd, J=2.1, 8.7, 2.4 Hz, 1H), 6.95-7.02 (m, 5H), 6.77 (d, J=8.7 Hz, 1H), 2.50 (t, 2H), 1.51-1.56 (m, 2H), 1.29-1.34 (m, 4H), 0.87 (t, 3H) ppm. $^{13}$C NMR (100 MHz, CD$_3$OD) δ 174.0, 166.8, 140.6, 136.6, 132.6, 131.6, 129.8, 129.3, 122.9, 120.2, 117.6, 36.1, 32.5, 32.2, 30.7, 23.4, 14.3 ppm.

5-[N-(4-hexylphenyl)sulfamoyl]-2-hydroxybenzoic acid (2d), synthesized using Method B, was obtained as an off white powder (54.7 mg, 60%); $^1$H-NMR (300 MHz, CD$_3$OD) δ 8.30 (d, J=2.4 Hz, 1H), 7.51-7.55 (2.1, 8.7, 2.4 Hz, 1H), 6.95-7.02 (m, 4H), 6.78 (d, J=8.7 Hz, 1H), 2.49 (t, 2H), 1.52 (m, 2H), 1.27 (m, 6H), 0.86 (t, 3H) ppm. $^{13}$C NMR (100 MHz, CD$_3$OD) δ 180.6, 174.4, 166.9, 140.7, 136.7, 132.8, 131.8, 130.1, 129.5, 123.0, 120.3, 117.9, 36.3, 32.9, 32.7, 30.1, 23.8, 14.5 ppm.

5-[N-(4-heptylphenyl)sulfamoyl]-2-hydroxybenzoic acid (2e), synthesized using Method B, was obtained as a colorless powder (58.0 mg, 46%); $^1$H-NMR (300 MHz, CD$_3$OD) δ 8.30 (d, J=3.0 Hz, 1H), 7.51 (dd, J=2.4, 8.7, 2.4 Hz, 1H), 6.94-7.02 (m, 5H), 6.77 (d, J=9.0 Hz, 1H), 2.48 (t, 2H), 1.52 (m, 2H), 1.26 (m, 8H), 0.87 (t, 3H) ppm. $^{13}$C NMR (100 MHz, CD$_3$OD) δ 180.3, 174.2, 166.8, 140.6, 136.5, 132.6, 131.7, 129.9, 129.4, 123.2, 122.8, 120.1, 117.7, 36.1, 32.9, 32.5, 30.2, 23.6, 14.4 ppm.

5-[N-(4-decylphenyl)sulfamoyl]-2-hydroxybenzoic acid (2f), synthesized using Method B, was obtained as a colorless powder (74.5 mg, 61%); $^1$H-NMR (300 MHz, CD$_3$OD) δ 8.31 (d, J=2.4 Hz, 1H), 7.56-7.53 (dd, J=2.4, 9, 2.1 Hz, 1H), 6.95-7.01 (m, 4H), 6.79 (d, J=8.4 Hz, 1H), 3.34 (s, 1H), 2.50 (t, 2H), 1.53 (m, 2H), 1.25 (m, 14H), 0.89 (t, 3H) ppm. $^{13}$C NMR (100 MHz, CD$_3$OD) δ 174.2, 166.8, 140.6, 136.5, 132.7, 131.7, 129.9, 129.5, 122.8, 119.9, 117.8, 36.2, 33.0, 32.5, 30.6, 30.5, 30.4, 30.2, 23.7, 14.4. ppm 5-[N-(4-dodecylphenyl)sulfamoyl]-2-hydroxybenzoic acid (2g), synthesized using Method B, was obtained as a colorless powder (140 mg, 40%); $^1$H-NMR (300 MHz, CD$_3$OD) δ 8.30 (s, 1H), 7.56 (d, J=7.8 Hz, 1H), 6.95-7.02 (m, J=8.4, 9 Hz, 5H), 6.80 (d, J=8.4 Hz, 1H), 2.51 (t, 2H), 1.52 (m, 2H), 1.27 (m, 16H), 0.94 (t, 3H) ppm. $^{13}$C NMR (75 MHz, CD$_3$OD) δ 167.02, 140.9, 136.7, 132.9, 131.9, 130.1, 129.7, 123.0, 118.0, 36.4, 33.3, 32.8, 30.9, 30.7, 30.5, 23.9, 14.6 ppm.

2-hydroxy-5-[N-(4-tetradecylphenyl)sulfamoyl]benzoic acid (2h), synthesized using Method B, was obtained as a colorless powder (98.2 mg, 72%); $^1$H-NMR (300 MHz, CD$_3$OD) δ 8.31 (d, J=2.1 Hz, 1H), 7.53 (dd, J=2.4, 8.7 Hz, 1H), 6.95-7.03 (m, 5H), 6.77 (d, J=8.7 Hz, 1H) ppm. $^{13}$C NMR (75 MHz, CD$_3$OD) δ 166.9, 140.7, 136.8, 132.8, 131.9, 130.0, 129.6, 123.0, 120.4, 117.8, 36.4, 33.3, 32.8, 30.9, 30.7, 30.5, 23.9, 14.7 ppm.

2-hydroxy-5-[N-(4-(4-methylpentyl)phenyl]sulfamoyl) benzoic acid (2i), synthesized using Method B, was obtained as a colorless powder (79.1 mg, 43%); $^1$H-NMR (300 MHz, CD$_3$OD) δ 8.31 (d, J=2.4 Hz, 1H), 7.54 (dd, J=2.4, 8.7 Hz, 1H), 6.98-7.01 (m, 5H), 6.79 (d, J=8.4 Hz, 1H), 2.49 (t, 2H), 1.57 (m, 3H), 1.17 (m, 2H), 0.84 (t, 6H) ppm. $^{13}$C NMR (100 MHz, CD$_3$OD) δ 166.8, 140.6, 136.5, 132.6, 131.7, 129.9, 129.4, 122.8, 120.1, 117.7, 117.1, 39.6, 36.4, 30.8, 30.3, 28.9, 22.9 ppm.

2-hydroxy-5-[N-(4-(5-methylhexyl)phenyl)sulfamoyl] benzoic acid (2j), synthesized using Method B, was obtained as an off-white powder (231 mg, 82%); $^1$H-NMR (300 MHz, CD$_3$OD) δ 8.34 (d, J=2.4 Hz, 1H), 7.57 (dd, J=2.4, 8.7 Hz, 1H), 6.98 (m, 4H), 6.80 (d, J=8.7 Hz, 1H), 2.49 (t, 2H), 1.93 (s, 1H), 1.41-1.50 (m, 3H), 1.09-1.26 (m, 5H), 0.82 (d, 6H) ppm. $^{13}$C NMR (75 MHz, CD$_3$OD) δ 174.5, 166.9, 140.7, 136.6, 132.8, 131.9, 130.1, 129.5, 123.0, 120.3, 118.1, 40.1, 36.4, 32.9, 29.2, 28.2, 23.2 ppm.

5-[N-(4-(3,3-dimethylbutyl)phenyl)sulfamoyl]-2-hydroxybenzoic acid (2k), synthesized using Method A, was obtained as an off-white powder (27.4 mg, 43%); $^1$H-NMR (300 MHz, CD$_3$OD) δ 8.29 (s, 1H), 7.53 (d, J=6 Hz, 1H), 6.91-7.02 (m, 5H), 6.80 (d, J=9.9 Hz, 1H), 2.45-2.51 (m, 2H), 1.38-1.44 (m, 2H), 0.85-0.99 (m, 1H), 0.93 (s, 9H) ppm. $^{13}$C NMR (75 MHz, CD$_3$OD) δ 166.9, 141.3, 136.5, 132.7, 131.8, 130.0, 129.9, 129.7, 129.5, 123.7, 123.1, 122.9, 47.4, 31.5, 31.2, 29.6 ppm.

2-hydroxy-5-[N-(4-phenethylphenyl)sulfamoyl]benzoic acid (2m), synthesized using Method B, was obtained as a colorless powder (75.1 mg, 53%); $^1$H-NMR (300 MHz, CD$_3$OD) δ 8.31 (d, J=2.4 Hz, 1H), 7.55 (dd, J=2.4, 8.4, 2.4 Hz, 1H), 7.02-7.20 (m, 5H), 6.95 (m, 4H), 6.80 (d, J=8.4 Hz, 1H), 2.77 (s, 4H) ppm. $^{13}$C NMR (75 MHz, CD$_3$OD) δ 180.4, 174.2, 166.8, 142.7, 139.5, 136.8, 132.6, 131.7, 130.1, 129.9, 129.5, 129.3, 129.1, 126.8, 122.7, 120.1, 117.8, 38.9, 38.3 ppm.

5-[N-(4-(2-cyclohexylethyl)phenyl)sulfamoyl]-2-hydroxybenzoic acid (2l), synthesized using Method B, was obtained as a colorless powder (135 mg, 45%); $^1$H-NMR (300 MHz, CD$_3$OD) δ 8.33 (d, J=2.4 Hz, 1H), 7.56 (dd, J=2.7, 8.7, 2.4 Hz, 1H), 6.90-6.99 (m, 4H), 6.80 (d, J=9 Hz, 1H), 2.45-2.51 (m, 2H), 1.64-1.72 (m, 5H), 1.33-1.42 (m, 2H), 1.10-1.26 (m, 4H), 0.85-0.93 (m, 2H) ppm. $^{13}$C NMR (75 MHz, CD$_3$OD) δ 174.5, 166.9, 141.0, 136.6, 132.8, 131.9, 130.1, 129.6, 123.0, 120.3, 118.0, 40.6, 38.6, 34.6, 33.7, 27.9, 27.6 ppm.

Methyl 5-[N-(4-butylphenyl)sulfamoyl]-2-hydroxybenzoate (7). Isolated as an intermediate in the synthesis of 1, ester 7 was obtained as a colorless solid (618 mg, 90% yield). $^1$H-NMR (300 MHz, CDCl$_3$) δ 8.30 (d, J=2.4 Hz, 1H), 7.82 (dd, J=8.7, 2.4 Hz, 1H), 6.97-7.00 (m, 4H), 6.96 (d, J=9.0 Hz, 1H), 3.88 (s, 3H), 2.49 (t, 2H), 1.47-1.52 (m, 2H), 1.21-1.31 (m, 2H), 0.87 (t, 3H) ppm. $^{13}$C NMR (75 MHz, CDCl$_3$) δ 169.4, 164.5, 140.3, 133.9, 133.7, 130.2, 129.6, 129.1, 122.1, 118.4, 112.1, 52.6, 34.8, 33.3, 22.1, 13.7 ppm.

Methyl 2-(2-amino-2-oxoethoxy)-5-(N-(4-butyl phenyl)sulfamoyl)benzoate (8). Ester 7 (311 mg, 0.86 mmol) and anhydrous Cs$_2$CO$_3$ (1.04 g, 4.28 mmol) were added to a solution of 2-iodoacetamide (161 mg, 1.72 mmol) in anhydrous acetone (6 mL). The reaction mixture was refluxed with vigorous stirring for 18 h. After cooling to room temperature, the reaction mixture was filtered and the filtrate evaporated under reduced pressure. The residue was dissolved in EtOAc (5 mL) and the solution was washed with 1 N HCl (2×5 mL), 0.5 N Na$_2$CO$_3$ (5 mL) and water (5 mL), dried over Na$_2$SO$_4$ and concentrated under reduced pressure. The crude product was purified by flash column chromatography with 60% EtOAc-hexanes, affording product 8 as a colorless powder (114 mg, 31% yield). $^1$H-NMR (300 MHz, CDCl$_3$) δ 11.30 (s, 1H), 8.14 (d, J=2.4 Hz, 1H), 7.48 (dd, J=2.4, 9.0 Hz, 1H), 7.13 (d, J=8.4 Hz, 1H), 7.01-6.96 (m, 4H), 6.62 (br s, 1H), 5.90 (br s, 1H), 4.23 (s, 2H), 2.58 (t, 2H), 1.51-1.61 (m, 2H), 1.28-1.37 (m, 2H), 0.92 (t, 3H) ppm. $^{13}$C NMR (75 MHz, CDCl$_3$) δ 170.3, 165.0, 143.6, 136.7, 134.6, 130.7, 129.4, 127.4, 118.5, 112.3, 54.4, 52.8, 35.0, 33.3, 22.2, 13.8 ppm.

5-[N-(4-butylphenyl)sulfamoyl]-2-(carbamoylmethoxy) benzoic acid (3). Ether 8 (43 mg, 0.10 mmol) was dissolved in 1:1:1 THF-MeOH—H$_2$O (9 mL) and crushed pellets of NaOH (107 mg, 2.68 mmol) were added to the stirring solution. After stirring for 18 h, the reaction mixture was concentrated under reduced pressure, diluted with water (5 mL) and washed with EtOAc (3×5 mL). The combined organic layers were washed with brine (5 mL), water (5 mL) and dried over Na$_2$SO$_4$ and concentrated under vacuum. Compound 3 (40.0 mg) was obtained in 98% yield as an off-white powder. $^1$H-NMR (300 MHz, CDCl$_3$) δ 8.02 (d, J=2.4 Hz, 1H), 7.64 (dd, J=2.4, 9.0, 2.1 Hz, 1H), 7.07-7.16 (m, 4H), 7.04 (d, J=8.7 Hz, 1H), 4.24 (s, 2H), 2.60 (t, 2H), 1.52-1.63 (m, 2H), 1.29-1.39 (m, 2H), 0.93 (t, 3H) ppm. $^{13}$C NMR (100 MHz, CDCl$_3$) δ 173.0, 172.9, 166.7, 144.5, 138.6, 135.6, 132.4, 130.1, 129.2, 119.0, 114.5, 54.7, 36.0, 34.6, 23.2, 14.1 ppm.

Isolation of HMG CoA Reductase

A clone containing the HMG-CoA reductase gene from *S. aureus* (mvaA) in a pET28 vector (Novagen) with an N-terminal 6x-His tag was transformed into competent BL21[DE3] cells grown to an OD of 0.6 and induced with 1.0 mM of IPTG. After 3 h of induction at 37° C. the cells were lysed with a French press. The resulting lysate was clarified by centrifugation at 50,000 rpm for 1 h, and the overexpressed protein isolated from the supernatant using a Talon column (Clonetech). After concentration, the protein was further purified using Sephacryl S200 (HiPrep 26/60 Pharmacea Biotech) equilibrated with the reaction buffer. The final protein solution was concentrated to 10 mg/ml for crystallization trials and subsequently diluted to 1 mg/ml for kinetic experiments.

Identification of Class II HMG-CoA Reductase Inhibitors

The kinetic studies were carried out in Corning 3695 96-well format plates with each experiment occupying a 6×4 grid of wells. Each of the wells contained a total volume of 200 μl of a solution containing Tris-HCl (100 mM), K2HPO4 (25 mM) and KCl (50 mM) at a pH of 7.5. HMG-CoA and NADPH were added to each well to achieve final concentrations of 150 at 300 μM, respectively. Reaction was initiated by the addition of purified HMGR (50 ng) using a multi-channel pipette and was followed by measuring the absorbance at 340 nm for 3 min at 10 s intervals using a BioTex Synergy H1 plate reader. The slope of the linear portion of this curve was taken as the rate, measured in milliOD/min.

Inhibitor was added to the wells at five different concentrations with fourfold redundancy. No inhibitor was added to one column of wells that served as a 100% control. The concentrations of inhibitor used were adjusted to bracket the 50% inhibition level, ensuring minimal errors between data points. The four redundant readings were averaged and the variation calculated to give a standard deviation. These values were graphed and the final IC$_{50}$ and its error bars determined.

Inhibition of HMG CoA Reductase and Bactericidal Activity

Inhibition of purified *S. aureus* HMGR by 1, 2a-m and 3 was assayed in parallel format by monitoring oxidation of NADPH to NADP$_+$ in the conversion of HMG CoA to mevalonate by monitoring change in absorbance at 340 nm using a 96-well plate reader. All experiments were performed in quadruplicate with IC$_{50}$ values determined by curve fitting. The IC$_{50}$ values of 1 and its analogues 2a-m and 3 are shown in Table 1.

In parallel with the inhibition studies, all molecules were also tested for the ability to inhibit growth of MRSA in culture. The minimum inhibitory concentration (MIC) and the minimum bactericidal concentration (MBC) of the HMG-CoA reductase inhibitors were tested in triplicate against methicillin-resistant *S. aureus* (MRSA) in a micro dilution method, according to Clinical and Laboratory Standards (CLSI) (Table 1). Similar tests against *E. coli*, which has the alternative MEP/DOXP isoprenoid biosynthesis pathway and therefore lacks HMGR, show no inhibitory effects of any of the compounds at the concentrations tested.

TABLE 1

Inhibition of *S. aureus* HMGR and Bactericidal Activity Against MRSA of Designed Analogues.

Figure 3:
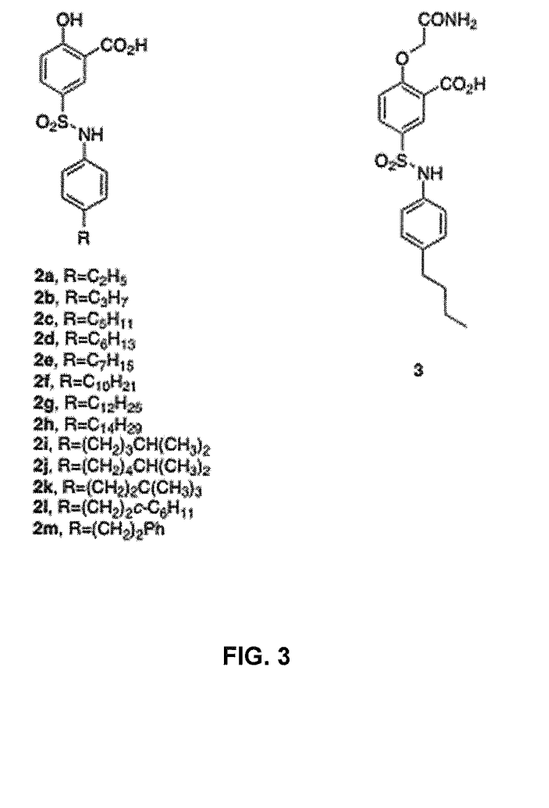
FIG. 3 shows the structures of compounds synthesized and tested for inhibitory activity.

| Analog | R$^a$ | cLogP$^b$ | IC$_{50}$, µM | MIC, µM | MBC, µM |
|---|---|---|---|---|---|
| 1 | C$_4$H$_9$ | 3.14 | 91 ± 5 | c | c |
| 2a | C$_2$H$_5$ | 2.22 | d | c | c |
| 2b | C$_3$H$_7$ | 2.68 | d | c | c |
| 2c | C$_5$H$_{11}$ | 3.61 | 98 ± 3 | c | c |
| 2d | C$_6$H$_{13}$ | 4.07 | 77 ± 6 | 128 | 128 |
| 2e | C$_7$H$_{15}$ | 4.54 | 28 ± 2.0 | 64 | 64 |
| 2f | C$_{10}$H$_{21}$ | 5.93 | 7.2 ± 0.6 | 16 | 16 |
| 2g | C$_{12}$H$_{25}$ | 6.86 | 5.9 ± 0.5 | 128 | 128 |
| 2h | C$_{14}$H$_{29}$ | 7.79 | 1.9 ± 0.15 | c | c |
| 2i | (CH$_2$)$_3$CH(CH$_3$)$_2$ | 3.95 | 36 ± 4 | 64 | e |
| 2j | (CH$_2$)$_4$CH(CH$_3$)$_2$ | 4.41 | 22 ± 1.0 | 64 | 64 |
| 2k | (CH$_2$)$_2$C(CH$_3$)$_3$ | 4.00 | d | c | c |
| 2l | (CH$_2$)$_2$c-C$_6$H$_{11}$ | 3.90 | 16.2 ± 10 | 32 | 32 |
| 2m | (CH$_2$)$_2$Ph | 3.49 | d | c | c |
| 3 | C$_4$H$_9$$^c$ | 1.88 | d | c | c |

$^a$Structures of 2a-m and 3 are shown in FIG. 3.
$^b$cLogP calculations were performed using OSIRIS Molecular Property calculator of Actelion labs.
$^c$No growth inhibition of MRSA was noted at any of the concentrations tested.
$^d$No significant inhibition of HMGR activity was observed at the concentrations tested.
$^e$Analogue 2i displayed bacteriostatic activity but no bactericidal activity.

Inhibition of HMGR increased with increasing length of the alkyl "tail", and hence with increasing lipophilicity. Conversely, truncation of the tail resulted in the loss of enzymatic inhibition. The C$_{14}$ tail of 2h afforded the greatest inhibition of HMGR (IC$_{50}$=1.9 µM), a 45-fold improvement over lead compound 1. However, when the bactericidal activity of these compounds was examined, it was found that activity was observed only for those compounds with a tail of C$_6$ or longer; moreover, whereas the C$_{10}$ analogue 2f exhibited an MBC of 16 µM—nearly comparable to its IC$_{50}$ of 7.2 µM—the analogues with longer tails (2g and 2h) lost bactericidal activity. Differences between enzymatic and bactericidal activity of these analogues may be attributable to the ability of these compounds to traverse the plasma membrane. The most lipophilic members 2g and 2h may lose activity owing to their localization within the membrane, thus suggesting that an optimal lipophilicity might be desirable for maximal bactericidal activity and that 2f best approximates that optimal value. Examination of calculated log P values (Table 1) suggests that an optimal value would lie in the range of 6-7.

The inhibitory activity of the branched-chain analogues 2i and 2j closely resembled that of their straight-chain counterparts. The IC$_{50}$ of 2j, with a branched-chain C$_7$ tail, is 22 µM, which is close to the IC$_{50}$ of the straight-chain C$_7$ analogue 2e of 28 µM. Likewise, their MBC values are both 64 µM. On the other hand, analogue 2k, with a tail containing a bulky t-butyl group, failed to exhibit any activity, suggesting that the bulky t-butyl group cannot be accommodated within the active site of HMGR. The analogue 2l with a terminal cyclohexyl substituent showed activity closely parallel to that of the comparably lipophilic alkyl analogue 2j but was the second-most bactericidal analogue. Interestingly, the terminal phenyl analogue 2m exhibited no enzymatic inhibition or bactericidal activity, perhaps indicating that the rigid phenyl ring couldn't be accommodated within the HMGR active site.

The analogue 3, in which the phenol had been O-alkylated with an acetamide group designed to engage Asn213 in a cooperative hydrogen bond, failed to show any enzymatic inhibition or bactericidal activity. The lack of bactericidal activity can be explained from the low log P value shown in Table 1, but the lack of enzymatic inhibition by 3 suggests that the alkylation of the phenol has removed the water-mediated hydrogen bond to Asn213 without a compensatory cooperative hydrogen bond.

Evaluation of HMG-CoA Reductase Inhibitors Against MRSA, VRE, and VRSA

The MIC and MBC of HMGR inhibitors against vancomycin resistant *Enterococcus faecalis* (VRE) ATCC 51299 and methicillin-resistant *Staphylococcus aureus* (MRSA) ATCC 43300 were tested in triplicate in a micro dilution broth method, using Muller Hinton broth (MHB) and 96 well plates, and according to CLSI. The MICs of compounds against vancomycin resistant *S. aureus* (VRSA) NARSA Strain ID VRS10 were tested in triplicate using a micro dilution broth method, using Tryptone Soya broth and 96 well-plate and according to CLSI. The bacterial cultures were incubated at 37° C. for 20 hours. The bacterial cultures were incubated at 37° C. for 20 hours. Results are presented in Tables 2 and 3.

TABLE 2

The MIC and MBC of HMG-CoA reductase inhibitors against vancomycin resistant *Enterococcus faecalis* (VRE) and methicillin-resistant *Staphylococcus aureus* (MRSA)

| Compound | VRE MIC/MBC | MRSA MIC/MBC |
|---|---|---|
| 2f | 32/32 | 16/16 |
| 2l | 64/64 | 32/32 |
| 2j | 128/128 | 64/64 |
| 2d | >128 | 128/128 |
| 2e | 64/64 | 64/64 |
| 2g | 128/128 | 128/>128 |
| 2k | 128/128 | >128 |
| 2i | 32/64 | 64/>128 |
| 2i pure | 128/>128 | 128/>128 |

TABLE 3

The MIC of HMG-CoA reductase inhibitors against VRSA

| Compounds name | VRSA MIC (µM) |
|---|---|
| 2f | 16 |
| 2l | 32 |
| 2j | 32 |

TABLE 3-continued

The MIC of HMG-CoA reductase inhibitors against VRSA

| Compounds name | VRSA MIC (μM) |
|---|---|
| 2e | 64 |
| vancomycin | >256 |

Evaluation of HMG-CoA Reductase Inhibitors Against Clinical Isolates

The MICs and MBCs of HMG-CoA reductase inhibitors against ten clinical isolates of MRSA and vancomycin intermediate *S. aureus* (VISA) isolates were tested in triplicate against 10 clinical methicillin-resistant *Staphylococcus aureus* (MRSA) and vancomycin intermediate *Staphylococcus aureus* (VISA) isolates in micro dilution broth method and according to CLSI. The bacterial cultures were incubated at 37° C. for 20 hours. Results are presented in Table 4.

TABLE 4

The MIC and MBC of HMG-CoA reductase inhibitors against clinical MRSA and VISA isolates

| Strain | 2f MIC/MBC (μM) | 2l MIC/MBC (μM) | 2j MIC/MBC (μM) | 2e MIC/MBC (μM) |
|---|---|---|---|---|
| VISA/NRS1 Vancomycin Intermediate *Staphylococcus aureus* | 4/4 | 16/16 | 16/16 | 16/16 |
| USA400/NRS123 | 4/16 | 16/16 | 16/32 | 32/32 |
| USA100/NRS382 | 8/8 | 16/16 | 16/32 | 32/32 |
| USA200/NRS383 | 4/4 | 16/16 | 16/32 | 16/32 |
| USA300/NRS384 | 4/8 | 16/16 | 16/32 | 32/32 |
| USA500/NRS385 | 4/8 | 16/16 | 16/16 | 16/16 |
| USA700/NRS386 | 4/8 | 16/16 | 16/16 | 32/32 |
| USA800/NRS387 | 4/8 | 16/16 | 16/32 | 16/32 |
| USA1000/NRS483 | 4/8 | 8/16 | 16/32 | 16/32 |
| USA1100/NRS484 | 4/8 | 16/16 | 16/32 | 16/32 |

Time-Kill Assays

The bactericidal effect of compound 2f was tested against MRSA in time-kill assays. Bacterial cells in the logarithmic growth phases were exposed to compound 2f concentrations equivalent to 1×, 2× and 3× MIC in MHB. Bacteria were cultured for 20 h. Colony forming units (cfu/mL) were determined after 0, 2, 4, 6, 8, and 10 h of incubation. The data is presented as the average of triplicates±standard deviations in FIG. 4. The data points without error bar indicate that standard deviation is too small to be seen.

Figure 4:
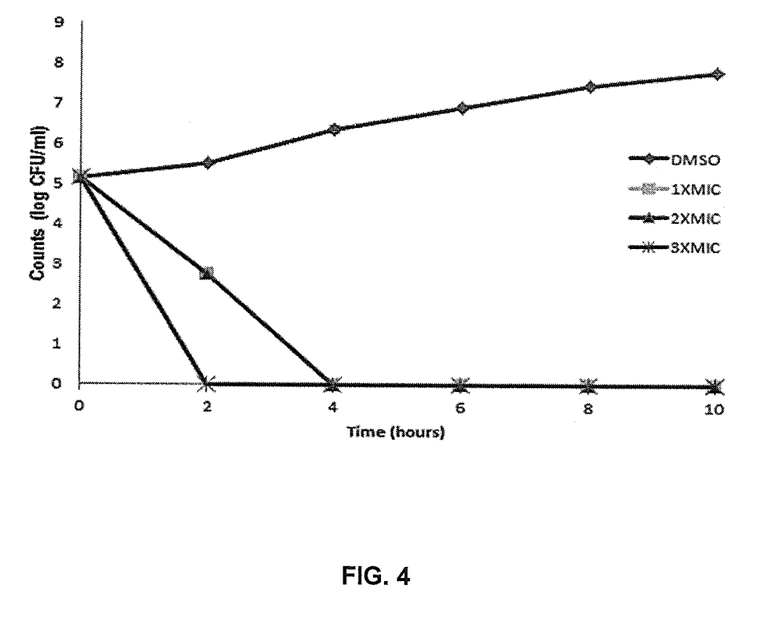
FIG. 4 is a representative time-kill curve of compound 2f against MRSA cultured in Mueller Hinton broth (MHB).

Treatment of MRSA with 3× MIC of compound 2f results in complete elimination of MRSA cells within a two-hour window. Treatment of MRSA with 1× MIC or 2× MIC of compound 2f reduces the MRSA cell count more gradually, with four hours are required to eliminate bacteria completely. Vancomycin treatment (3× MIC) failed to reduce the number of CFU by 3-$\log_{10}$ within a 10 hour window. These results indicate that compound 2f is better than vancomycin at eliminating MRSA cells. This information is clinically relevant as it would impact the size and timing of the dose given to patients with MRSA infections.

In Vitro Cell Viability/Cytotoxicity Studies

Cytotoxicity of the compounds was evaluated using J774A.1 cells (mitochondrial function) in the CellTiter 96® AQ$_{ueous}$ Non-Radioactive Cell Proliferation Assay (Promega). The assay measures the bioreduction of 3-(4,5-dimethylthiazol-2-yl)-5-(3-carboxymethoxyphenyl)-2-(4-sulfophenyl)-2H-tetrazolium (MTS) to formazan by metabolically active cells. Formazan is measured by measuring the absorbance at 490 nm. Briefly, ~2×10$^4$ J774A.1 cells suspended in 200 μL DMEM supplemented with 10% fetal bovine serum (FBS), L-glutamine, NaHCO$_3$, pyridoxine-HCl, and 45,000 mg/L glucose and preserved with 1% penicillin-streptomycin solution were seeded in 96-well plates and incubated at 37° C. in a 5% CO$_2$ atmosphere. The cells were cultured for 24 hours (60% confluency) before the assays. The J774A.1 cells were further incubated with 100 μM of compounds (2f, 2l, 2j, and 2e) and DMSO as a control for 24 hours. The culture media was discarded, and the cells in each well were washed with PBS and re-suspended with 100 μL of cell culture media prior to addition of the assay reagent. The plates were incubated for 4 hours at 37° C. in a humidified 5% CO$_2$ atmosphere. The absorbance at 490 nm was recorded using a 96-well Elisa plate reader (SoftMax ProInc., USA). Results were expressed as the percentage mean absorbance by cells upon incubation with various treatments (compounds 2f, 2j, 2i, and 2e) with respect to incubation with DMSO. The results are expressed as means from six measurements±SD.

Figure 5:
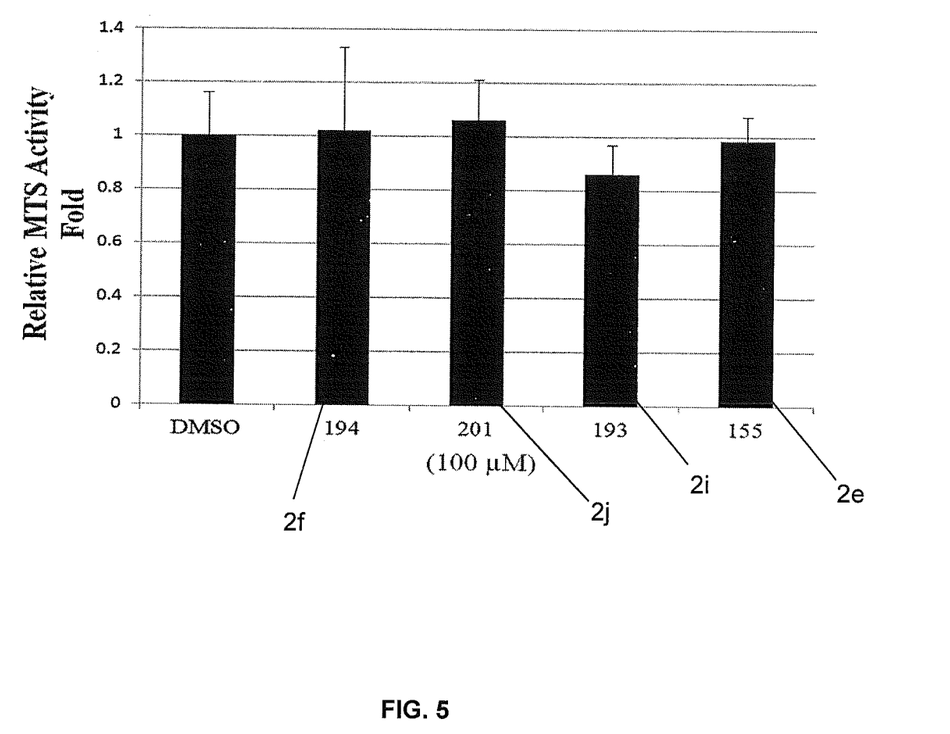
FIG. 5 presents the results of cytotoxicity assays showing the percent mean absorbance at 490 nm after incubating J774A.1 cells with various compounds.

MTS assays conducted on compounds 2f, 2j, 2i, and 2e and DMSO control at concentrations of 100 μM showed no significant differences in percentage mean absorption between various treatments (FIG. 5), indicating that the compounds are not toxic in vitro at this concentration.

Testing Class II HMGR Inhibitors Against MRSA and VRE Using a Live-Animal Infection Model

*Caenorhabditis elegans* worms were infected with MRSA (1500 adults worms) and VRE (1500 adults worms) for 15 hours. Infected worms were treated for 16 hours with 100 μM compounds (2f, 2l, and 2e) or DMSO. Vancomycin (100 μM) was used as a control for MRSA and linezolid (100 μM) was used as a control for VRE. After treatment, infected worms were washed five times with M9 buffer and 400 mg of 1.0-mm silicon carbide particles (Biospec Products, Bartlesville, Okla.) were added to each tube, the tubes were vortexed at maximum speed for one minute, which disrupts the worms but does not affect bacterial survival, and the resulting suspension was diluted and plated on tryptic soy agar containing kanamycin to select for MRSA and VRE. The results, presented in Tables 5 and 6, indicate that class II HMGR inhibitors are more effective in treating worms infected with MRSA or VRE than vancomycin or linezolid, respectively. None of the compounds affected the survival of uninfected *C. elegans*.

Statistical Analysis

All statistical analyses were performed using the Student two-tailed t-test using MICROSOFT EXCEL. P values<0.05 were considered significant.

TABLE 5

Treatment of *C. elegans* infected with MRSA

| Treatment | Log CFU/worm | Log Reduction |
|---|---|---|
| DMSO control | 5.04 ± 0.10 | 0.00 |
| 2f | 2.33 ± 0.09 | 2.71* |
| 2l | 2.20 ± 0.43 | 2.84* |
| 2e | 1.80 ± 0.10 | 3.24* |
| Vancomycin | 3.26 ± 0.20 | 1.78* |

TABLE 6

Treatment of *C. elegans* infected with VRE

| Treatment | Log CFU/worm | Log Reduction |
|---|---|---|
| DMSO control | 4.90 ± 0.01 | 0.00 |
| 2f | 0.70 ± 0.37 | 4.20* |
| 2l | 0.43 ± 0.68 | 4.47* |
| 2e | 0.86 ± 1.03 | 4.04* |
| Linezolid | 1.47 ± 0.06 | 3.43* |

Values represent the mean ± standard error numbers of CFU in triplicates. Statistical significance levels were defined as P < 0.01 (shown by asterisks).

Evaluation of HMG-CoA Reductase Inhibitors Against Other Bacterial Species Species Antimicrobial activities of compounds 2f and 2j were initially screened at 100 µM concentration against Gram-positive species *Bacillus anthracis* Sterne strain (34F2), *Bacillus subtilis*, *Bacillus cereus*, and *Listeria monocytogenes* and Gram-negative species *Brucella abortus*. Both compounds showed inhibition of growth at 100 µM concentration and were tested further to determine the MIC and MBC in micro dilution broth method, using MHB and according to CLSI. The results are presented in Table 7.

TABLE 7

MIC and MBC for compounds 2f and 2j against bacterial species.

| Compounds | *Bacillus anthracis* MIC/MBC | *Bacillus subtilis* MIC/MBC | *Bacillus cereus* MIC/MBC | *Listeria monocytogenes* MIC/MBC | *Brucella abortus* |
|---|---|---|---|---|---|
| 2f | 16/16 | 16/16 | 16/16 | 64/>128 | 128 |
| 2j | 32/32 | 32/32 | 64/64 | 128/>128 | 64 |

Evaluation of HMG-CoA Reductase Inhibitors Against Fungal Species

Antifungal activities of 22 HMG-CoA Reductase inhibitors were initially tested at 100 µM concentration against *Candida albicans* ATCC 18804. The compounds that showed any inhibition of growth at 100 µM concentration were tested further to determine the MIC and minimum fungicidal concentration (MFC) in micro dilution broth method, using yeast medium broth (YM).

TABLE 8

MIC and MFC for compounds against *Candida albicans*

| Compounds | *Candida albicans* MIC/MFC |
|---|---|
| 2f | 16/16 |
| 2j | 128/>128 |
| 2e | 64/128 |

Bactericidal Activity of HMG-CoA Reductase Inhibitors in an Adherent-Cell Biofilm An adherent biofilm for susceptibility testing was formed using a clinical isolate of *Staphylococcus aureus* (ATCC 6538). *S. aureus* biofilms were prepared in a tissue culture non-treated polystyrene 96-well plate (Corning) and washed with phosphate-buffered saline (PBS) to remove unbound bacteria. Subsequently, serial twofold dilutions of the compounds in MHB were added to wells containing adherent organisms. The polystyrene plates were incubated for 20 h at 37° C. The MIC was taken as the lowest drug concentration at which observable growth was inhibited. To determine the MBC, the MHB containing antibiotics was removed from each well and replaced with antibiotic-free MHB; the plates were incubated again for 20 h at 37° C. in air. The MBC was taken as the lowest concentration of each drug that resulted in no bacterial growth following removal of the compounds.

TABLE 8

Antimicrobial activities of the compounds against *Staphylococcus aureus* ATCC 6538 planktonic and adherent cells

| | Activity against | | | |
|---|---|---|---|---|
| | Planktonic organisms (not in biofilm) | | Adherent organisms (biofilm) MIC$^b$ | |
| Compound | MIC (µM) | MBC (µM) | (µM) | MBC$^b$ (µM) |
| 2f | 16 | 16 | 64 | 128 |
| 2j | 64 | 64 | 128 | 128 |
| 2d | 128 | 128 | 128 | >128 |
| 2i | 128 | 128 | 128 | 128 |
| 2e | 64 | 64 | 64 | 128 |
| Vancomycin | NA | NA | 2 | 8 |
| Linezolid | NA | NA | 4 | 16 |

The invention claimed is:

1. An inhibitor of Class II 3-hydroxy-3-methylglutaryl-coenzyme A reductase having one of the following structures:

wherein:

R$^1$=is a hydroxyl;

R$^2$=is H;

D is CR$^4$ wherein R4 is (CH2)$_m$R$^C$, wherein m=6-14 and R$^C$ is H;

A, B, E, X, Y, and Z are each CH;

or a pharmaceutically acceptable salts thereof.

2. An inhibitor according to claim 1, the inhibitor having antimicrobial activity against one or more bacterial or fungal pathogens.

3. The inhibitor of claim 2, wherein the bacterial pathogen is a Gram-positive pathogen.

4. The inhibitor of claim 2, wherein the pathogen is selected from the group consisting of *Bacillus anthracis*, *Bacillus subtilis*, *Bacillus cereus*, *Listeria monocytogenes*, *Brucella abortus*, *Candida albicans*, *Staphylococcus aureus*, *Enterococcus faecalis* and *Streptococcus pneumoniae*.

5. The inhibitor according to claim 2, wherein the pathogen is resistant to vancomycin and/or methicillin.

6. An inhibitor according to claim 1, wherein the inhibitor exhibits no toxicity or low toxicity toward mammalian cells.

7. The inhibitor of claim 1, wherein the inhibitor is 5-[N-(4-hexylphenyl)sulfamoyl]-2-hydroxybenzoic acid.

8. The inhibitor of claim 1, wherein the inhibitor is 5-[N-(4-dodecylphenyl)sulfamoyl]-2-hydroxybenzoic acid.

9. The inhibitor of claim 1, wherein the inhibitor is 2-hydroxy-5-[N-(4-tetradecylphenyl)sulfamoyl]benzoic acid.

10. A pharmaceutical composition comprising:
a pharmaceutically acceptable excipient; and
a compound according to claim 1.

11. A method of treating a multicellular organism infected with a bacterial or fungal pathogen comprising administering to the organism the pharmaceutical composition of claim 3 in an amount effective to kill or inhibit growth of the pathogen.

12. The method of claim 11, wherein the organism is a human.

13. A biocide comprising:
a diluent; and
a compound according to claim 1.

14. A method of disinfecting a surface comprising or at risk for comprising planktonic or adherent pathogenic bacteria comprising contacting the surface with an effective amount of the biocide of claim 13 for a period of time sufficient to kill or inhibit growth of the bacteria.

* * * * *